(12) United States Patent
Reime

(10) Patent No.: US 10,254,132 B2
(45) Date of Patent: Apr. 9, 2019

(54) SENSOR ARRANGEMENT AND METHOD FOR DETERMINING AT LEAST ONE PHYSICAL PARAMETER

(71) Applicant: Gerd Reime, Bühl (DE)

(72) Inventor: Gerd Reime, Bühl (DE)

( * ) Notice: Subject to any disclaimer, the term of this patent is extended or adjusted under 35 U.S.C. 154(b) by 68 days.

(21) Appl. No.: 15/106,334

(22) PCT Filed: Dec. 19, 2014

(86) PCT No.: PCT/EP2014/003442
§ 371 (c)(1),
(2) Date: Jun. 20, 2016

(87) PCT Pub. No.: WO2015/090609
PCT Pub. Date: Jun. 25, 2015

(65) Prior Publication Data
US 2017/0003144 A1 Jan. 5, 2017

(30) Foreign Application Priority Data

Dec. 20, 2013 (DE) .................. 10 2013 226 887
May 23, 2014 (DE) .................. 10 2014 007 491

(51) Int. Cl.
*G01B 7/02* (2006.01)
*G01D 5/20* (2006.01)
(Continued)

(52) U.S. Cl.
CPC ........... *G01D 5/2006* (2013.01); *G01B 7/023* (2013.01); *G01B 7/28* (2013.01); *G01D 5/24* (2013.01);
(Continued)

(58) Field of Classification Search
CPC ........... G01D 5/2006; G01D 5/24; G01B 7/28
See application file for complete search history.

(56) References Cited

U.S. PATENT DOCUMENTS 4,725,777 A 2/1988 Tousch
5,045,789 A 9/1991 Inoue
(Continued)

FOREIGN PATENT DOCUMENTS

DE 19521266 C1 2/1997
DE 10118819 A1 10/2002
(Continued)

OTHER PUBLICATIONS

German Office Action for corresponding application 10 2013 226 887.4 , dated Nov. 23, 2016.
(Continued)

*Primary Examiner* — Jermele M Hollington
*Assistant Examiner* — Feba Pothen
(74) *Attorney, Agent, or Firm* — Cantor Colburn LLP

(57) ABSTRACT

A sensor arrangement for determining at least one physical parameter of a sensor unit which is activated by at least one periodic excitation, comprising a detection region in which changes of the parameter in the surroundings of the sensor unit lead to an output signal from the sensor unit. The sensor unit is wired such that if there is no change of the parameter in the detection region the output signal is a zero signal at the output of the sensor unit, whereas if there are changes of the parameter in the detection region the output signal is a signal that is not zero and which has a specific amplitude and phase. By means of a closed-loop control, the non-zero signal in the receive path is adjusted to achieve an adjusted state at zero even in the presence of changes of the parameter in the detection region. Inherent in the control signal used for this adjustment is a deviation ($\Delta x$, $\Delta y$) of the control signal from the adjusted state, which deviation represents information about the parameter. To create a sensor arrangement and a method in which values of a physical parameter in a detection region can be clearly determined, in a four- (Continued)

quadrant representation of the deviation ($\Delta x$, $\Delta y$) in the form of a vector analysis in a phase space of the control signal, the angle of an imaginary vector (2.6) relative to the x axis of an x, y coordinate system, said vector leading from the origin (2.7) of the x, y coordinate system to a measuring point (2.5) and said origin corresponding to the adjusted state, represents a measurement for the change of the parameter along a direction, and/or the magnitude of the imaginary vector (2.6) represents a measurement for the change of the parameter along a further direction.

35 Claims, 10 Drawing Sheets

(51) Int. Cl.
| | | |
|---|---|---|
| *G01N 27/02* | (2006.01) | |
| *H03K 17/95* | (2006.01) | |
| *G01B 7/28* | (2006.01) | |
| *G01D 5/24* | (2006.01) | |
| *G01N 27/22* | (2006.01) | |
| *G01N 27/72* | (2006.01) | |
| *H03K 17/955* | (2006.01) | |

(52) U.S. Cl.
CPC ........... *G01N 27/028* (2013.01); *G01N 27/22* (2013.01); *G01N 27/72* (2013.01); *H03K 17/9502* (2013.01); *H03K 17/952* (2013.01); *H03K 17/955* (2013.01); *H03K 17/9525* (2013.01); *H03K 2217/94031* (2013.01)

(56) References Cited

U.S. PATENT DOCUMENTS

| | | | |
|---|---|---|---|
| 2002/0093338 A1 | 7/2002 | Rowan | |
| 2003/0160617 A1* | 8/2003 | Rowan | G01V 3/104 324/329 |
| 2004/0232234 A1* | 11/2004 | Zvezdine | G01D 5/145 235/449 |
| 2007/0126420 A1 | 6/2007 | Graze | |
| 2008/0223931 A1* | 9/2008 | Spiess | G06K 7/0008 235/439 |
| 2008/0284554 A1* | 11/2008 | Schroeder | G01B 7/003 336/200 |
| 2009/0076769 A1* | 3/2009 | Tokita | G01D 3/022 702/150 |
| 2012/0206138 A1 | 8/2012 | Derungs | |
| 2014/0117980 A1* | 5/2014 | Ely | G01D 5/2046 324/207.17 |

FOREIGN PATENT DOCUMENTS

| | | |
|---|---|---|
| DE | 10254697 A1 | 6/2004 |
| DE | 102012001202 A1 | 2/2013 |
| WO | 2012104086 A2 | 8/2012 |
| WO | 2013119741 A1 | 8/2013 |

OTHER PUBLICATIONS

Translation of German Office Action for corresponding application 10 2013 226 887.4, dated Nov. 23, 2016.
International Search Report for corresponding application PCT/EP2014/003442 filed Dec. 19, 2014; dated Mar. 13, 2015.
Rick Zarr, "Redefining inductive sensing", Electronic Design, May 13, 2013, Retrieved from Internet; URL; http://www.penton.com/digitaleditions/ed/ed120513_de.pdf, XP055173520.

* cited by examiner

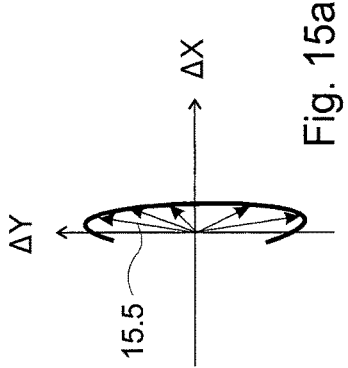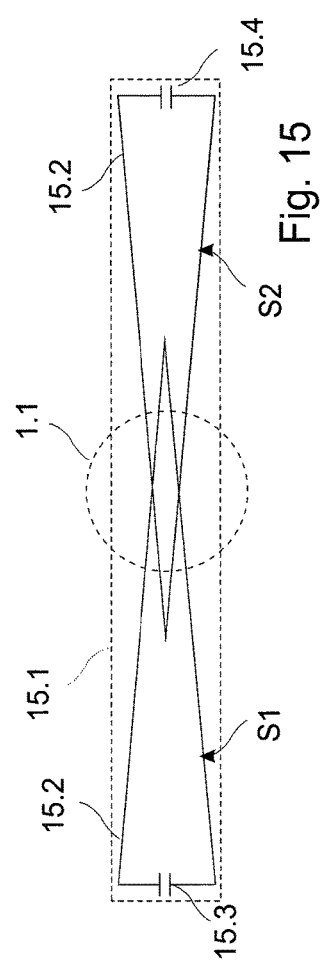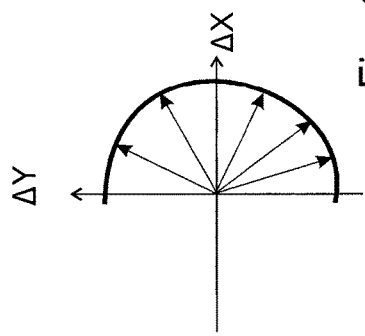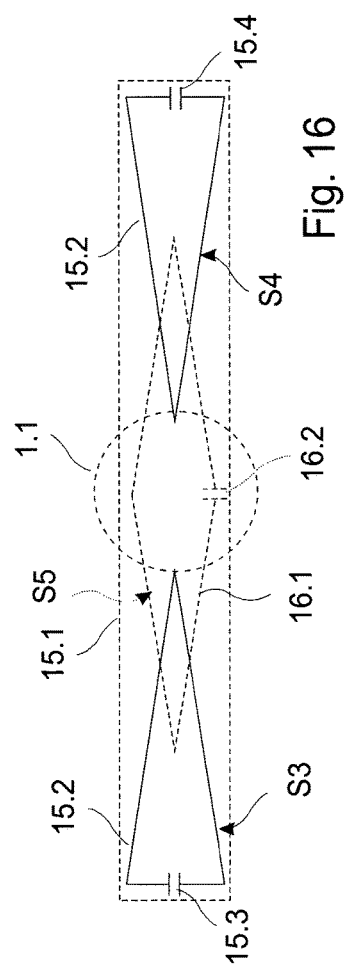

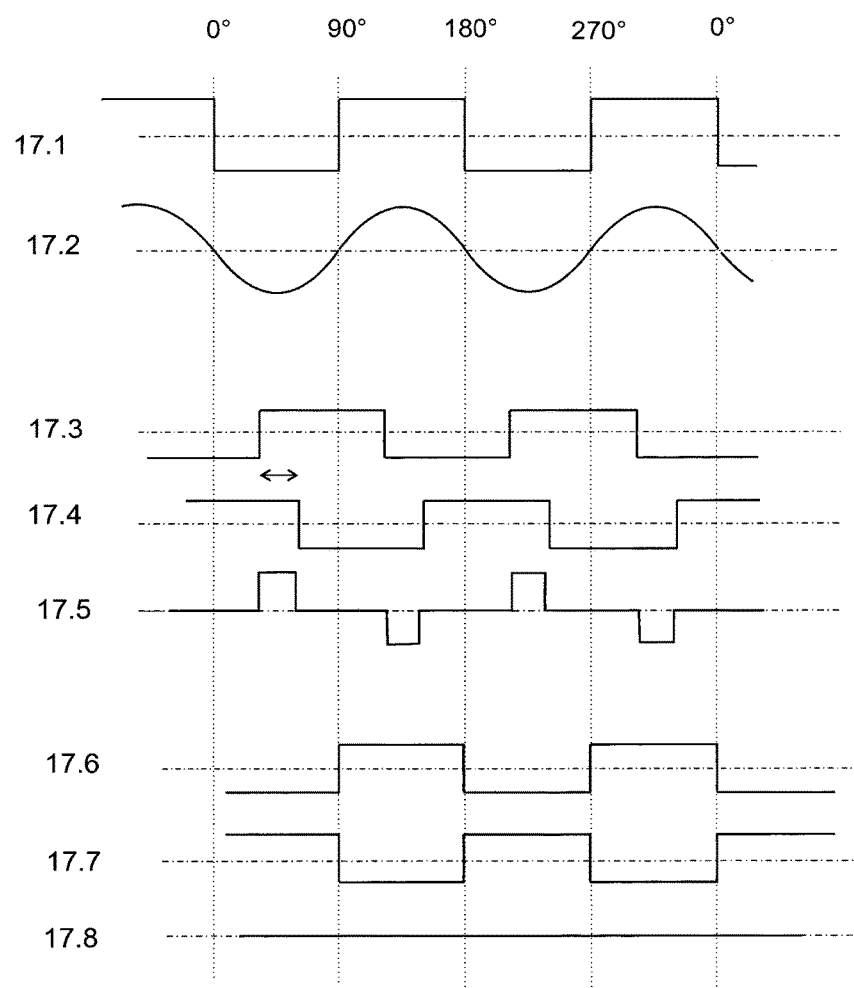
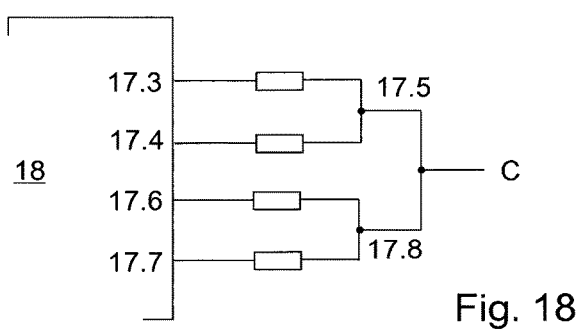
Fig. 17
Fig. 18

SENSOR ARRANGEMENT AND METHOD FOR DETERMINING AT LEAST ONE PHYSICAL PARAMETER

REFERENCE TO RELATED APPLICATIONS

The present invention relates to and claims the priority of German patent application 10 2013 226 887.4, filed on Dec. 20, 2013, and German patent application 10 2014 007 491.9, filed on 23 May 2014, the disclosure of which is hereby expressly incorporated by reference into the subject matter of the present application.

FIELD OF THE INVENTION

The invention relates to a sensor arrangement and a method for inductive or capacitive detection of at least one target by determining at least one physical parameter.

BACKGROUND

The most diverse methods for determining at least one physical parameter by means of a sensor unit are known from the prior art. These measurement methods frequently have in common a dependence on temperature, which is explained below with reference to inductive and capacitive measuring systems, provided the physical measured value is converted to an electrical value.

WO 2012/104086 A1 discloses a method for locating metal or metal-containing objects and materials, this method controlling currents in at least two transmitting coils in relation to one another such that a received signal that is received by at least one receiving coil, or mean values of demodulation phases generated from the received signal, are continuously controlled in relation to one another to give a zero value even when influenced by metal. In this case, the control values are detected as values at least at 0° and 90° and are taken into account in the calculation thereof such that an exact analysis of the metal objects located in the detection region is achieved. With this method, although a metal object can be analyzed, movements of the object in a particular direction of measurement cannot be unambiguously recognized. German patent application DE 10 2012 001 202 A1 describes a sensor comprising a coil arrangement in which the normally circular windings of a coil are configured in a meandering shape. Two transmitting coils and one receiving coil cooperate such that the received signal becomes zero. In this case, a respective transmitting coil is preferably arranged above and below the receiving coil. These transmitting coils have angles of rotation that are slightly different from the receiving coil, so by way of the distribution of transmitted currents the signal in the receiving coil can be controlled to give a zero value.

BRIEF SUMMARY

Taking this as a starting point, the disclosure provides a sensor arrangement and a method with which unambiguous conclusions can be drawn about values of a physical parameter in a detection region.

The invention results from considerations that are explained below by the example of an inductive proximity sensor, even though the method can also be used for a capacitive measurement as desired, provided the physical measured value is converted to an electrical value. Typically, electrical values delivered by a sensor of this kind are very small, so that an amplification or corresponding signal processing is performed before these signals can be evaluated. Although today's A/D converters in microprocessors are already very sensitive in order to convert an analogue signal into a digital signal, in some sensors the occurring changes in value are so small, yet still have to be detected, that it is beyond the capability even of an A/D converter of this kind. The invention takes as its starting point the fact that it is possible to compensate such a small signal by a signal that is just as small but entirely digitally generated, to give a zero value. This "zero signal" can then be amplified to any desired level and supplied to the A/D converter of the microprocessor. If this zero signal is kept constantly at zero by a closed-loop control, external influences and hence changes in amplification in the system that are caused thereby no longer have any influence on the control value.

The invention is substantially based on the realization that the signal that is determined in the receive path simultaneously contains information on the physical parameter and, in the exemplary embodiment, the shape and/or composition of the target or the size of the surface of the target in the detection region of the coil system.

In principle, the deviation in the control value also contains an item of information on the physical parameter, such as its distance from the sensor arrangement. This item of information is not available separately from other information on the physical parameter, however. Thus, in the case of the movement or the position of a target, the information on the distance from the sensor arrangement is overlaid by information on a movement of the target in a direction transverse to that of the distance. Here, in the case of an embodiment according to claim 4 or 18, the movement or position of the target are determinable by the change in shape and/or the change in composition, independently of the distance from the target to the coil system. If this information is processed in accordance with the claim, the desired further information on the physical parameter can consequently be deduced in a differentiated manner. As known from the prior art, continuous control of the signal in the receive path takes place in a closed-loop control circuit, such that the received signal is always controlled to give a zero value. Thus, a change in the detection region of the transmitting/receiving coil system always results in a change in the control signals. Thus, a deviation from the compensated condition, as an item of information for detection of the physical parameter such as the position of the target, is inherent in the control signal.

If, once the control variables have been calculated, the deviation thereof from a compensated initial condition is applied to a four-quadrant presentation in the form of a vector analysis in a phase space of the control signal, then according to the invention it is possible to establish that, in a four-quadrant presentation, the angle of an imaginary vector with the horizontal axis of a coordinate system, wherein the vector leads from the origin of the coordinate system corresponding to the compensated condition to a measurement point, is a measure of the change in the parameter in one direction and/or the magnitude of the imaginary vector is a measure of the change in the parameter in a further direction. In the case of the preferably performed detection of the position of a target in a direction of measurement, the angle that the imaginary vector makes with the horizontal axis is a measurement of the movement of the target in the direction of measurement, while the magnitude of the imaginary vector is a measure of the distance of the target normal to the direction of measurement. Thus, the movement/position of the target in the direction of measurement can be inferred separately from the distance/movement of the target normal to the direction of measurement, or, depending on the target, the composition and the shape of the target can be inferred.

This has the advantage that, for example in the case of rotating shafts and other rotational bodies having a conical, rotationally symmetrical shape, a movement along the axis of rotation can be detected separately from movements taking place in a direction transverse to this axis of rotation. Thus, distances and tolerances can be filtered out of the measurement result, provided the target is located in the detection region of the transmitting/receiving coil system.

Preferably, possible directions of measurement are all the directions of coordinate measuring systems. Here, the target can be constructed to be arcuate or indeed rotationally symmetrically conical, and/or may be mounted on the surfaces of a body whereof the movement is to be detected. In principle, any desired shape or composition is usable provided a change in the target in the direction of measurement has an effect on a coil system.

In the case of rotational bodies, there is moreover the possibility of observing the rotational body in the entire angular range, either with a plurality of targets that are mounted on the rotational body offset in respect of their angular position, or with a plurality of transmitting/receiving coil systems that are associated with and connected to a target.

If a plurality of targets is provided, these may have different resonant frequencies. In other words, the individual targets take a form such that they affect the signature in the vector plot such that their movement is unambiguously evaluable. Preferably, the targets taper in the direction of measurement, wherein the taperings of the targets are preferably arranged in opposite directions. This has the result that, when the target is moved, the inductive signature in the four-quadrant presentation leaves a larger track that can be better utilized for evaluating the movement and distance of the target from the transmitting/receiving coil system. If conductor tracks and in particular resonant circuits are used as targets, the inductive signature can be affected even further thereby, and a sensitivity that is higher by up to a factor of 20 than in the main patent can be achieved.

The term "zero signal" may be understood to mean a signal which, other than any noise present, contains no information at all. In particular, this may be understood to mean, in the case of alternating voltage, that no phase or indeed amplitude is present. In particular in this context, a direct current voltage and/or a noisy direct current voltage may also be understood as a zero signal. As a special case, a signal of 0 volts could also be understood as a zero signal.

Further advantages are apparent from the subclaims and the description given below of preferred exemplary embodiments.

BRIEF DESCRIPTION OF THE FIGURES

The invention is explained in more detail below with reference to an exemplary embodiment. In the Figures:

FIGS. 15, 16 show different exemplary embodiments of arrangements of a target above a transmitting/receiving coil system, in plan view, FIGS. 15a, 16a show inductive signatures that are obtained on the basis of the respective target, in a four-quadrant presentation of the system deviations Δx, Δy, FIG. 17 shows signal profiles in the course of controlling the received signal from the transmitting/receiving coil system to give a zero value, and FIG. 18 shows a schematic illustration relating to signal processing.

DETAILED DESCRIPTION OF PREFERRED EXEMPLARY EMBODIMENTS

The invention is now explained in more detail by way of example, with reference to the attached drawings. However, the exemplary embodiments are only examples, which are not intended to restrict the inventive concept to a particular arrangement. Before the invention is described in detail it should be pointed out that it is not restricted to the respective constituent parts of the device and the respective method steps, since these constituent parts and method steps may vary. The terms used here are merely intended to describe particular embodiments and are not used restrictively. Moreover, where the singular or the indefinite article is used in the description or the claims, this also refers to a plurality of these elements unless the overall context unambiguously indicates otherwise.

Here, the invention is explained below with reference to the example of an inductive proximity sensor, even though the method can also be used for any inductive or capacitive principles of measurement as desired, provided the physical measured value is converted to an electrical value. For this, the transmitting/receiving coil system 1.1 in the Figures would merely have to be replaced by a sensor unit that operates in a correspondingly different way.

Figure 1:
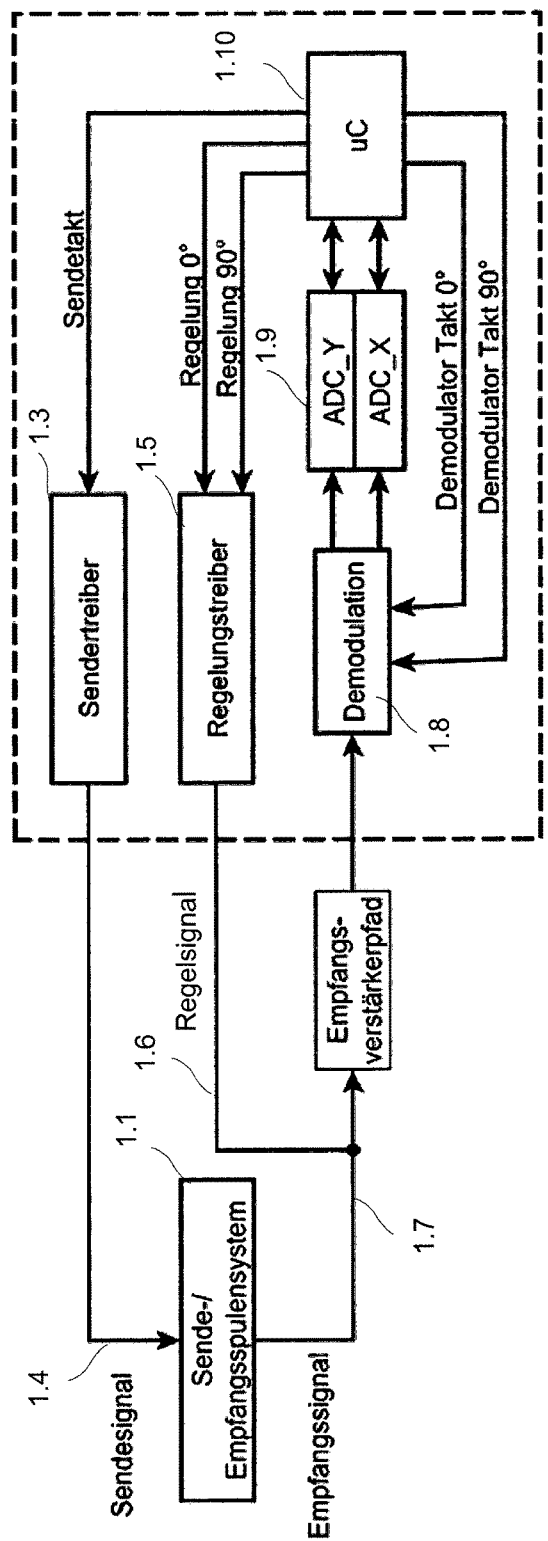
FIG. 1 shows a schematic block circuit diagram of the system components.

The underlying structure of the inductive sensor arrangement is illustrated in the block circuit diagram according to FIG. 1. This basic structure corresponds substantially to the construction known from WO 2012/104086 A1.

Figure 3:
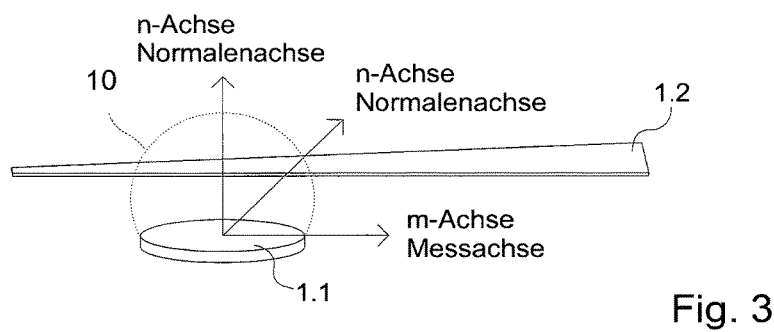
FIG. 3 shows a three-dimensional side view of a target with an associated transmitting/receiving coil system.

In an inductive proximity sensor, for the purpose of determining at least one physical parameter such as of at least one target 1.2, which is illustrated in FIGS. 3 to 9b, 11, 12, at least one transmitting/receiving coil system 1.1 is provided as part of the sensor arrangement. In the exemplary embodiment, for example the position or the type of material of the target is detected. The transmitting/receiving coil system 1.1 creates a detection region 10 as illustrated in FIG. 3. A transmission driver 1.3 delivers a periodic excitation in the form of a transmitted signal 1.4, preferably at a transmission frequency of for example 200 kHz, to the transmitting coil of the transmitting/receiving coil system 1.1. The transmitted signal of the transmitting/receiving coil system may for example be a square or sinusoidal signal. The transmitting/receiving coil system is of a geometric shape and/or is calibrated such that when there is no target in the detection region the received signal that is emitted from the transmitted signal 1.4 is zero. In the exemplary embodiment of FIG. 1, a target in the detection region 10 brings about an inductive effect of a signal not equal to zero in the receive path 1.7 of the transmitting/receiving coil system 1.1, this signal having a particular amplitude and phase.

The construction of the transmitting and receiving coil may be for example as in German patent application DE 10 2012 001 202 A1. Here, the normally circular windings of a coil are substantially configured in a waveform shape such that the received signal becomes zero. Therein the transmitting coil is offset slightly from the receiving coil at a rotational angle such that by way of the distribution of transmitting currents the signal in the receiving coil can be controlled to give a zero value. This coil system thus comprises at least two independent coil parts. The concrete circuit of the transmitting/receiving coil systems is further discussed below in conjunction with FIGS. 13, 14*a* and 14*b*.

As regards the amplitude and phase, and as regards the concrete construction of the transmitting/receiving coil system with transmitting coil and receiving coil, the reader is referred to the explanation in WO 2012/104086 A1. To summarize, that document makes it clear that the transmitted signal 1.4 has a periodic clock frequency as a result of the transmission clock signal, with the result that a target 1.2 in the detection region 10 brings about an amplitude and phase that can be determined by demodulation 1.8 at 0° (and 180°) and at 90° (and 270°). During demodulation, the amplitude portions in the exemplary embodiment are associated with the two clock phases of the transmission clock signal. Therein it is not important where exactly the demodulation phases are in relation to the transmission clock signal, but only that the demodulation phases are offset from one another by 90°. These DC signals, obtained from the demodulation phases, are measured for example using an analogue-to-digital converter 1.9, and are transferred to the microcontroller 1.10. The microcontroller 1.10 drives the control driver 1.5 in a closed-loop control circuit such that a control signal 1.6 is delivered to the receive path 1.7 such that the signal in the receive path 1.7 is zero. The signal in the receive path 1.7 may be amplified to almost any desired extent before demodulation, since in principle only the deviation from the compensated condition is present in the signal.

Signal preparation and the interpretation of the measured values, and control, are implemented by the microcontroller 1.10. The transmission driver 1.3, control driver 1.5, demodulation 1.8 and analogue-to-digital converter 1.9 may be constructed externally or, with a suitable microcontroller having suitable peripherals, be formed internally in the microcontroller. The components illustrated inside the dashed frame in FIG. 1 may hence be a constituent part of the microcontroller.

By means of its control signal 1.6, the control driver 1.5 always ensures that a signal not equal to zero which is triggered in the receive path, for example by a target 1.2, is compensated to zero. The control signal accordingly exactly replicates in its phase and amplitude the electromagnetic effect of the target 1.2 on the transmitting/receiving coil system. Here, a deviation $\Delta x$, $\Delta y$ from the compensated condition, as an item of information for detection of the position of the target, is inherent in the control signal 1.6. This item of information can then be evaluated accordingly.

Figure 4A:
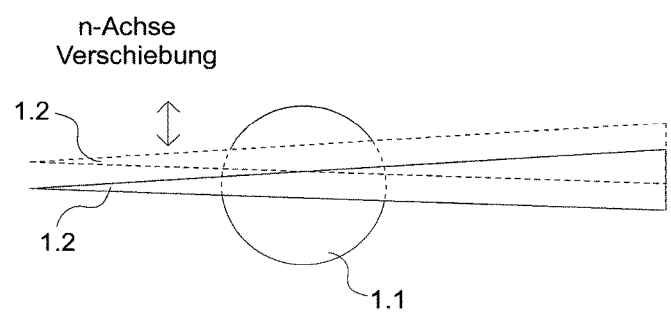
FIGS. 4a, 4b show a plan view of the illustration according to FIG. 3, with the target displaced along the n axis and with the target displaced along the measurement axis m.
Figure 4B:
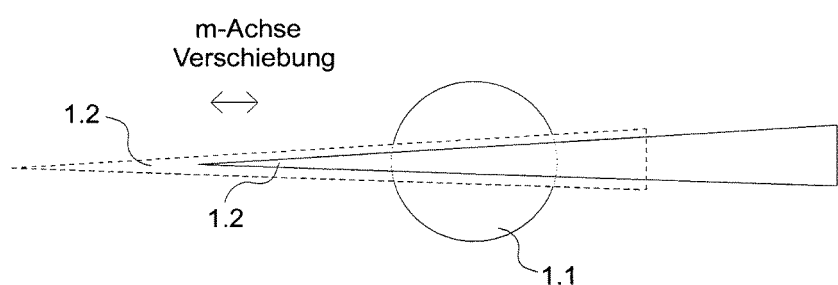

According to FIGS. 3 and 4*a*, 4*b*, for this purpose there is used as the measurement variable that acts on the inductive signature—that is to say acting thereon in the manner in which for example the deviations $\Delta x$ and $\Delta y$ appear in a four-quadrant presentation—by way of example a shape of target 1.2 that varies in a direction of measurement m. If the only important criterion is the distance from the measurement arrangement, the target may also take a homogeneous form.

FIGS. 3, 4*a*, 4*b* relate to a target 1.2 that tapers in or in opposition to a particular direction of measurement m. Instead of the tapering of the target, other shapes and inhomogeneous compositions or material combinations that have an effect on the inductive signature are also conceivable. For example, the target may also change its shape in steps in the direction of measurement m. It is also conceivable for the composition of the target 1.2 to change in the direction of measurement m, because for example an inhomogeneous composition is used. The only important criterion is that, as in the exemplary embodiment in FIG. 1, the transmitting/receiving coil system 1.1, which is formed by at least two coils, has a detection region 10 and is connected such that in the absence of the influence of metal in the detection region the output signal at the output of the transmitting/receiving coil system 1.1 is a zero signal. If there is a target 1.2 in the detection region 10, the output signal is a signal that is not equal to zero and has a particular amplitude and phase. In a closed-loop control circuit, this signal that is not equal to zero is compensated to give a zero value by means of a control signal 1.6 even in the presence of the target 1.2 in the detection region 10, for the purpose of achieving a compensated condition. In this case, a deviation $\Delta x$, $\Delta y$ of the control signal from the compensated condition, as distance information for detection of the position of the target 1.2, is inherent in the control signal 1.6. In other words, the control deviations contain information on the physical parameter that is not unambiguously attributable. These deviations $\Delta x$, $\Delta y$ of the control signal are applied to an x, y coordinate system in a four-quadrant presentation in the form of a vector analysis in a phase space of the control signal, wherein the origin 2.7 of the x, y coordinate system corresponds to the compensated condition of the transmitting/receiving coil system 1.1 in which the control signals are zero or are calibrated to zero. The change in the control signal, which is discussed in more detail below, has the result that, in the four-quadrant presentation of the deviation $\Delta x$ and the deviation $\Delta y$ of the control signal, the angle that an imaginary vector 2.6 that leads from the origin 2.7 to a measurement point 2.5 makes with the x axis of the x, y coordinate system is a measure of the movement of the target 1.2 in the direction of measurement m, that is to say a measure of the value of the physical parameter in a direction or along a scale. Further, the magnitude of the imaginary vector 2.6 is a measure of the distance of the target 1.2 normal to the direction of measurement m, that is to say a measure of the value of the physical parameter in a further direction or along a further scale.

Before this is discussed in more detail, first of all the method sequence will be explained with reference to the flow diagram according to FIG. 2. Once the system has been started, in step 100, first a calibration is performed, and where appropriate compensation is performed, according to step 101. For this, first the values of the analogue-to-digital converter 1.9 are input in step 102. Depending on the measured values, a check is performed in step 103 as to whether compensation is required. Hence, the microcontroller 1.10 specifies values for the control driver 1.5 in step 104 in order to compensate for any tolerances in the system. This procedure is carried out for both phases of the transmission clock signal until the values of the A/D conversion reach a predetermined value, for example the center of the dynamic range of the A/D converter. Typically, this procedure lasts only a few milliseconds. Thereafter, the tolerances of the coil system and any environmental influences are compensated. If the result in step 105 is then that calibration is required, the measured values of the A/D conversion are stored in step 106 and from then on serve as the calibrated zero point of the system.

Now the actual measurement begins, that is to say that the effect of the target 1.2 on the inductive system is measured. This effect gives the deviation Δx and Δy from the calibrated zero point according to step 108. From these deviations it is possible to determine the inductive signature, that is to say a measure of the position or movement of the target 1.2 in the direction of measurement m, according to step 109, and a measure of the distance of the target 1.2 from the compensated condition normal to the direction of measurement m, according to step 110. These values can be cross-referenced in a look-up table, a table of values according to step 111, in order for example to identify the composition of the material. However, they also serve to determine the position, shape and distance of the target 1.2 in the directions of measurement. The values determined in this way can then be displayed according to step 112. The method runs continuously, that is to say that after step 112 the system jumps back to step 102. This continuous control ends only when the system is taken out of service.

Returning to FIG. 3, a structure having a wedge-shaped, tapering target and a transmitting/receiving coil system 1.1 is shown. The coordinate system m, n, n is applied in this application such that, taking the transmitting/receiving coil system 1.1 as a starting point, the m axis defines a change in position in this system on a measurement axis, while a change in position on one of the n axes is a change in the position of a target extending normal to this measurement axis. A movement along one of the n axes thus changes the distance of the target 1.2 from the transmitting/receiving coil system. The two n axes are hence normal to the m axis. FIG. 3 shows a three-dimensional side view of a system of this kind; FIGS. 4a, 4b show a plan view. A movement of the target 1.2 into the area illustrated in dashed lines in FIG. 4a is thus a movement along the n axis, and shows for example a displacement relative to the transmitting/receiving coil system 1.1, transversely in relation to the m axis. By contrast, a movement according to FIG. 4b is a movement in the direction of the m axis, which is preferably the direction of measurement.

The target 1.2 is illustrated only schematically in the Figures. Within certain limits, for measurements in the direction of measurement, the m axis, the measuring system is independent of tolerances relating to the n axis. If a rotationally symmetrical, conical target is used instead of a wedge-shaped one, the system is moreover entirely insensitive to rotational deviations about the m axis, while changes along the m axis can still be measured.

Figure 5:
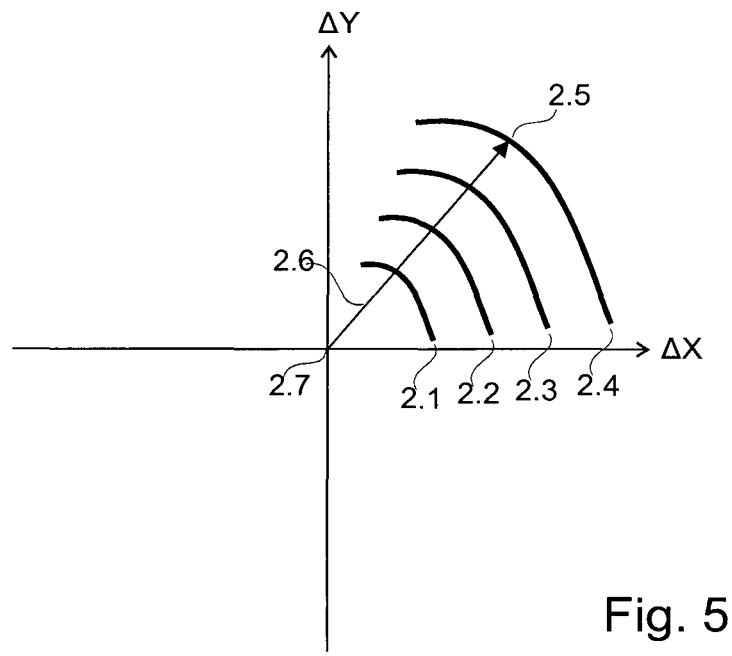
FIGS. 5, 6 show a four-quadrant presentation of the deviations of the control signals.
Figure 6:
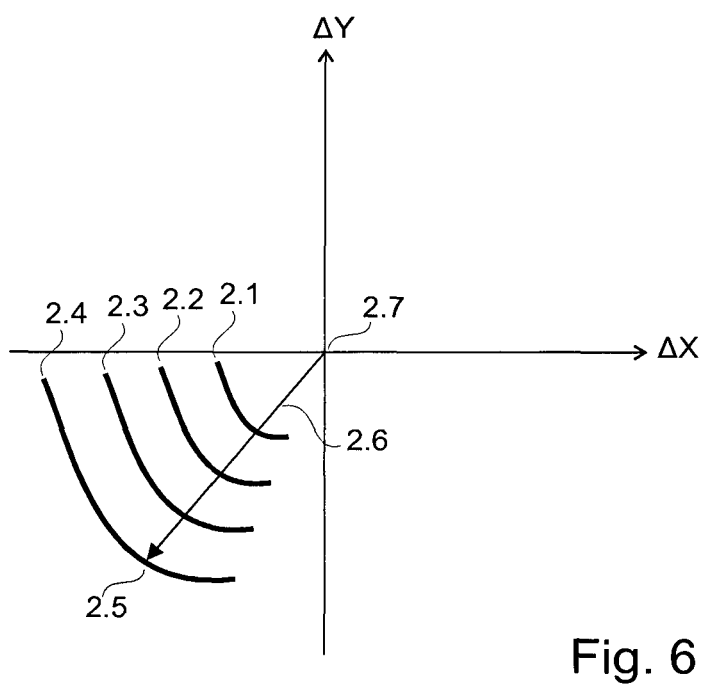

This is clear from FIGS. 5 and 6, which show the signals applied to a four-quadrant presentation. The measured value curves 2.1 to 2.4 result from passing a wedge-shaped target through the detection region 10, along the m axis, with four different distances from the m axis. It can be seen that as the distance becomes smaller, the curve of the position from measured value curve 2.1 to measured value curve 2.4 moves away from the origin 2.7. The curve 2.1 thus shows the signal profile with a large distance from the target to the sensor, and the curve 2.4 shows the signal profile with a small distance from the target to the sensor. At the same time, it can be seen that the curves are scaled. If the target 1.2 is displaced in the direction of measurement m without a displacement in a direction normal to the direction of measurement m, such as in the direction of the n axis, the direction of an imaginary vector 2.6, or the angle between the x axis and an imaginary vector 2.6 from the origin 2.7 to the measurement point 2.5, changes. Thus, the direction of the vector exclusively represents a measurement of the movement of the target 1.2 in the direction of measurement m. In practice, this means for example that a target having a length of approximately 50 mm and a tapering from 7 mm to 2 mm brings about a change in the angle that the vector makes with the x axis from 21.5° to 46.2°.

If there is a movement normal to the direction of measurement m, and hence in the n direction, without a displacement along the m axis, the magnitude of the imaginary vector 2.6 from the origin 2.7 to the measurement point 2.5 changes. The magnitude of the vector in this case describes the distance of the target from the coil system. The direction of the vector, which describes the inductive signature, remains the same, however. Thus, the magnitude of the vector represents exclusively the position of the target, that is to say the distance from the target to the coil system.

The signal profile shown in FIG. 5 is only exemplary. In the case of targets of different materials or shapes, signals may also be produced in other quadrants or with different target-specific signal profiles. Thus, for example, FIG. 6 shows application to the third quadrant.

Figure 2:
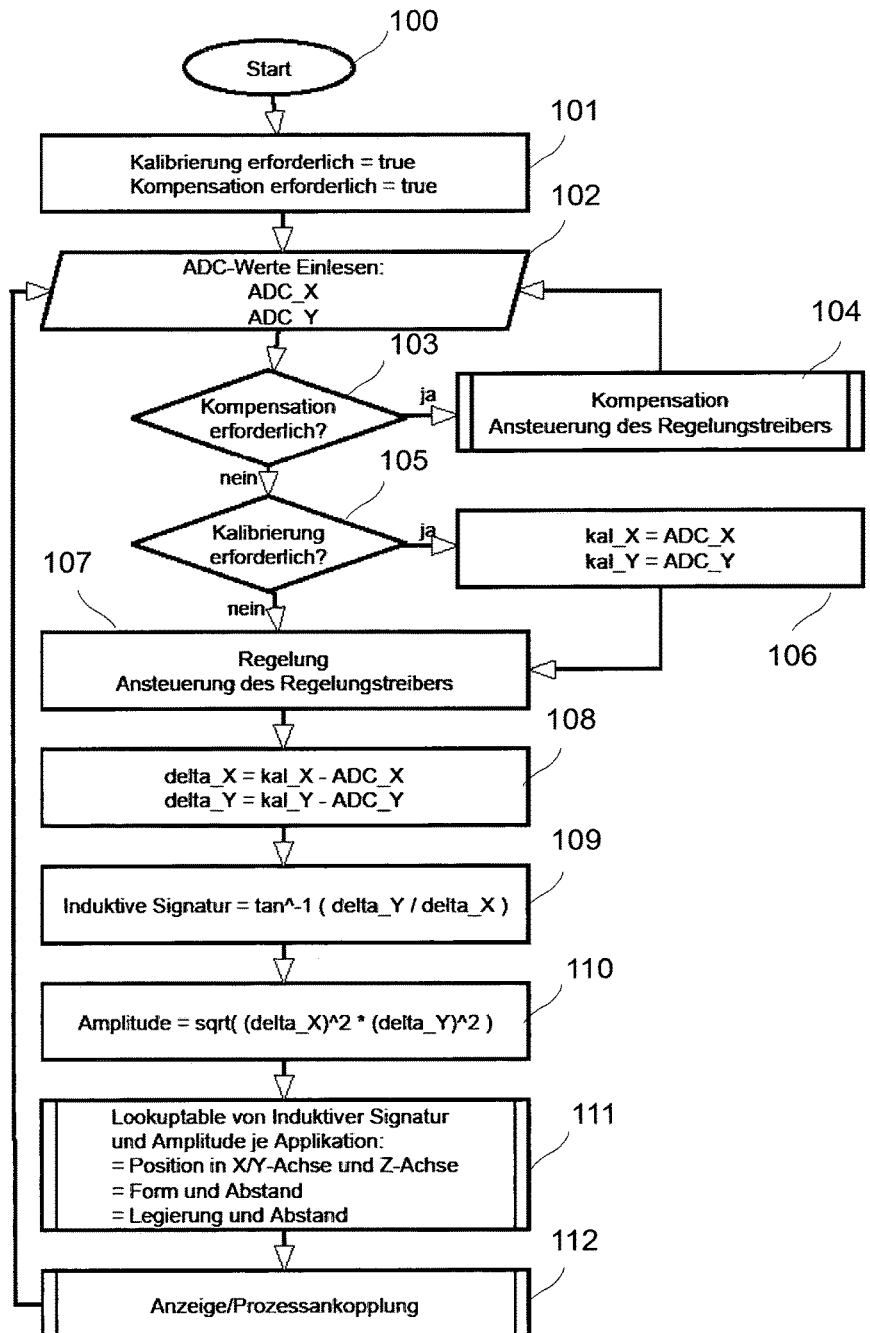
FIG. 2 shows a flow diagram of the procedure when evaluating the measured value.

In order to identify from these illustrations the position and distance of the target 1.2 in relation to the coil system, the deviations Δx, Δy of the control signal that are determined according to FIG. 2 are interpreted such that in step 108 the magnitude of the vector $B_v$ is produced from the root mean square of the deviations from the calibrated zero point, that is to say:

$$B_v = \sqrt{\Delta X^2 + \Delta Y^2} \qquad \text{Formula 1}$$

This magnitude of the value corresponds to the distance of the target 1.2 from the coil system. The position of the target along the m axis is produced from the direction of the imaginary vector 2.6:

$$S_i = \tan^{-1}\left(\frac{\Delta Y}{\Delta X}\right) \qquad \text{Formula 2}$$

$S_i$ represents the inductive signature and corresponds to the position along the m axis. The values $B_v$ and $s_i$ may be used as numerical values in further applications. Using special algorithms that are generated for the corresponding application, or a table of values generated therefor in which standard values of amplitude and inductive signature are stored, different measurement variables may be inferred according to step 111, depending on the application. Possible measurement variables are for example:

the position of a target along the m axis, and the distance from the m axis the composition and distance of a target the shape and distance of a target The first measurement variable ($S_i$) is determined by the direction of the imaginary vector 2.6, or its angle with the x axis, and the second measurement variable ($B_v$) is determined by the magnitude of this vector.

Figure 7:
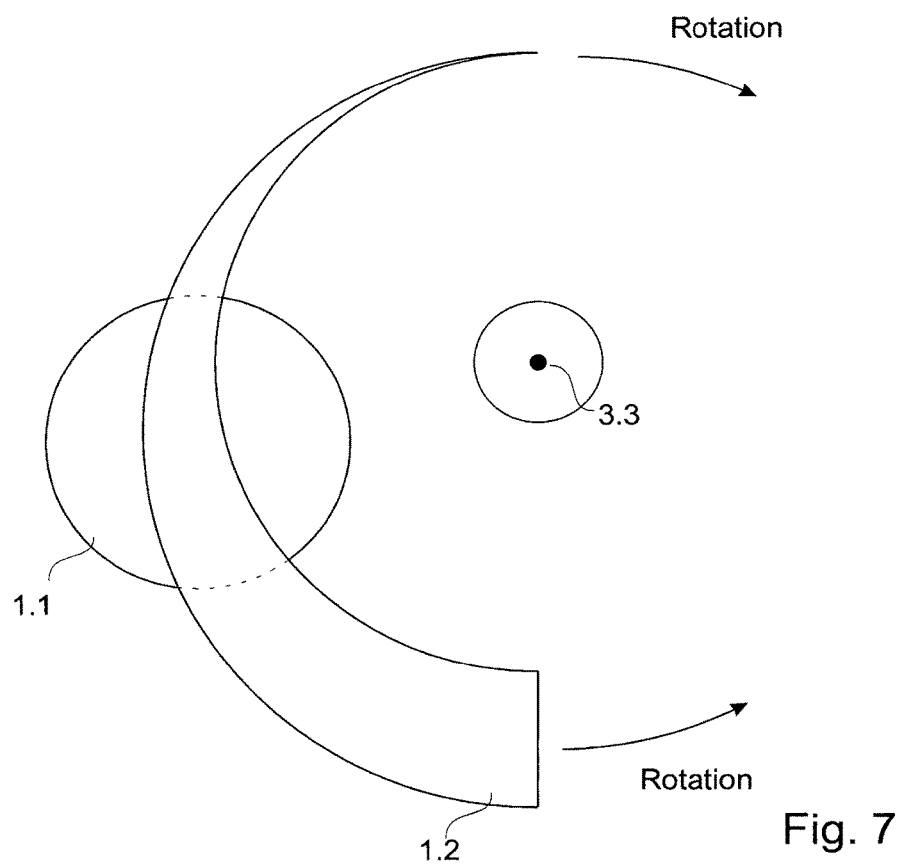
FIGS. 7, 8 show a plan view and a side view of the target and transmitting/receiving coil arrangement with a rotating target.
Figure 8:
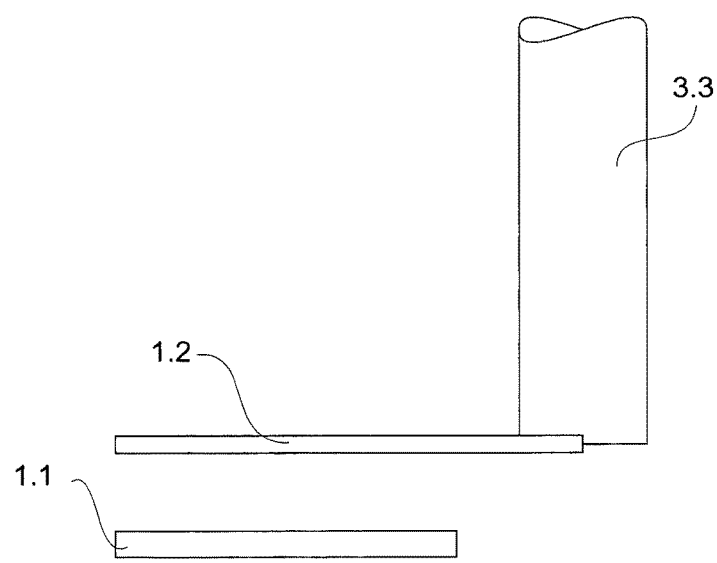

The structure illustrated in FIG. 3 may also be implemented as a rotating system, according to FIGS. 7 and 8. Here, a tapering arcuate target 1.2 is rotated above the coil system 1.1 about an axis of rotation 3.3. Within certain limits, this measuring system is once again independent of displacement tolerances occurring parallel and/or normal to the axis of rotation 3.3.

Figure 9A:
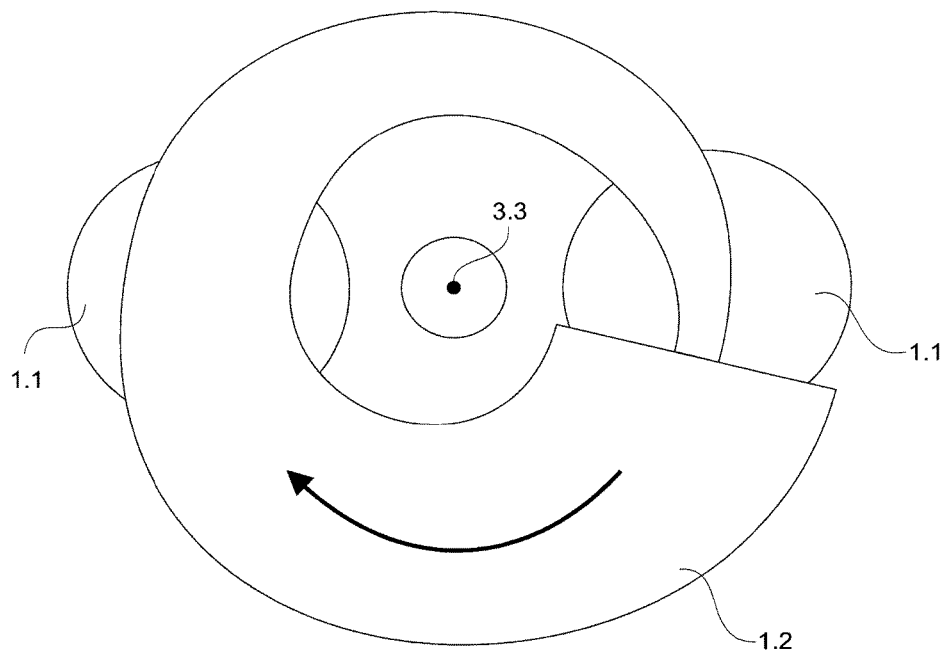
FIGS. 9a, 9b show illustrations according to FIG. 7, in an exemplary embodiment having two transmitting/receiving coil systems.
Figure 9B:
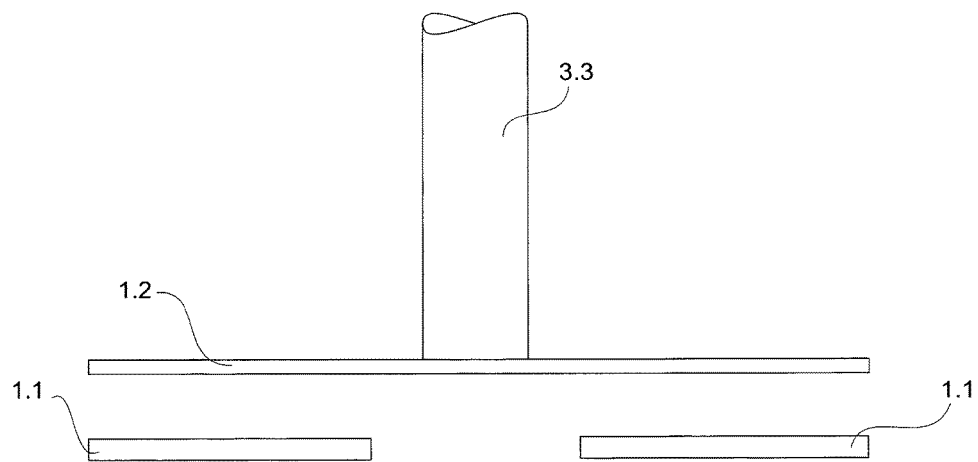

So that rotations about 360° can be detected without gaps in a case of this kind, the target 1.2 can be structured according to FIGS. 9a, 9b. Here, the tapered end of the target adjoins the other end of the target. For this purpose, for example at least two transmitting/receiving coil systems 1.1 may be used so that signal jumps produced at the transition from the beginning to the end of the target 1.2 cannot result in misinterpretations. The signals that are produced at different rotational angle positions of the target 1.2 when measuring with two transmitting/receiving coil systems are illustrated schematically in FIG. 10. A first transmitting/receiving coil system generates a first signal profile 5.1, and a second transmitting/receiving coil system generates a second signal profile 5.2. During measurement, when a switchover point 5.3 is reached, there may be a switchover between evaluation of the first and the second signal profile, to prevent misinterpretations at the jump points 5.4 of the signals. In FIGS. 9a, 9b, the two transmitting/receiving coil systems 1.1 are arranged opposite one another in respect of the axis of rotation 3.3.

Figure 11:
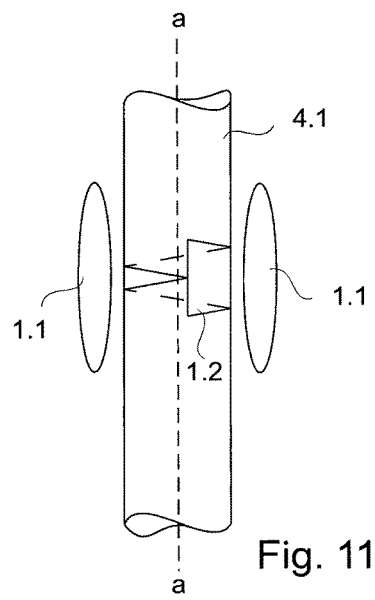

The overall arrangement and the method may also be used to measure the rotation of a rotational body 4.1, such as a shaft. FIG. 11 shows a structure of this kind for measuring the rotation of a shaft. Within certain limits, this system is also independent of displacement tolerances occurring parallel and/or at a right angle to the axis of rotation a-a of the rotational body, since here too movement in the direction of measurement m can be detected separately from a movement normal to the direction of measurement n.

Figure 10:
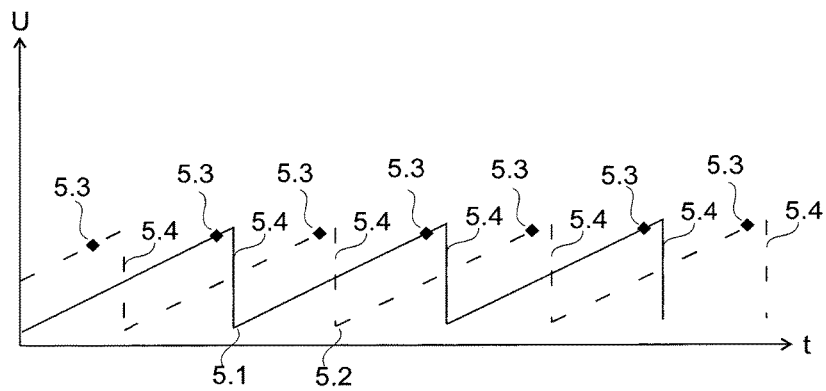
FIG. 10 shows signal profiles of the two transmitting/receiving coil systems according to FIGS. 9a, 9b, FIGS. 11, 12 show different embodiments of the sensor arrangement for detecting the rotation of a shaft.

So that rotations about 360° can be detected without gaps, here too two transmitting/receiving coil systems 1.1 are used so that signal jumps produced at the transition from the beginning to the end of the target cannot give rise to misinterpretations. In the concrete exemplary embodiment, the transmitting/receiving coil systems are located diametrically opposite one another. The target 1.2 is mounted on the periphery of the rotational body 4.1 and preferably extends over the entire periphery of the rotational body, tapering along the periphery. Similarly, the target 1.2 may have a different shape or composition along the periphery of the rotational body 4.1. As a result of the two transmitting/receiving coil systems 1.1, a signal profile as presented in FIG. 10 is produced.

Figure 12:
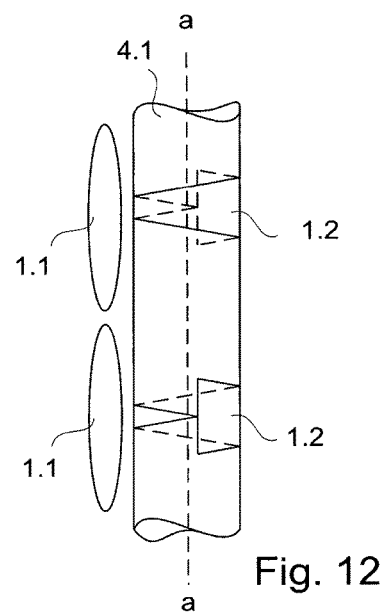

In order to make it possible in an alternative manner for both transmitting/receiving coil systems 1.1 to be able to be mounted on only one side of the rotational body 4.1, a structure according to FIG. 12 may be created. In this case, a plurality of targets 1.2 are mounted offset spatially and in respect of their angular position on the rotational body 4.1. Within certain limits, this measuring system is also independent of displacement tolerances occurring parallel and/or at a right angle to the rotational body.

Using this system, the torsion at a rotational body 4.1 such as a shaft can also be measured. If in fact two transmitting/receiving coil systems are provided at different points on the axis of rotation of the rotational body, differences in the signals of the two measuring systems correspond to a torsion of the shaft. As the measuring variable, axial play or wear on a rotating shaft as the rotational body may also be determined. This measuring variable is in fact mirrored in the distance of the target 1.2 from the transmitting/receiving coil system 1.1 as the total magnitude $B_v$, and can be detected clearly separately from the position of the target, as the inductive signature $S_i$.

According to the method, the position of a target is detected with an inductive sensor arrangement having a transmitting/receiving coil system 1.2 constructed with at least two coils and having a detection region 10. The transmitting/receiving coil system 1.1 is connected or indeed geometrically shaped and/or calibrated such that the output signal at the output of the transmitting/receiving coil system is a zero signal when there is no metal influence in the detection region 10. When there is a target 1.2 in the detection region 10, the output signal is a signal not equal to zero, this signal having a particular amplitude and phase. By way of a closed-loop control circuit having a control signal 1.6 acting on the receive path, a control driver 1.5 controls the signal not equal to zero to give a zero value even when the target 1.2 is present in the detection region 10, for the purpose of achieving a compensated condition. Deviations Δx, Δy from the compensated and calibrated condition respectively are inherent in this control signal, as an item of information on distance for detecting the position of the target. These deviations Δx, Δy of the control signal are applied to a four-quadrant presentation in an x, y coordinate system whereof the origin is the compensated or calibrated condition, that is to say the condition in which the control signal is zero. If the target 1.2 has a shape or composition that varies in a direction of measurement m, then the item of information is evaluated in the four-quadrant presentation of the deviations Δx, Δy of the control signal, wherein the angle of an imaginary vector 2.6 from the origin 2.7 to a measurement point 2.5 is taken as a measure of the movement of the target 1.2 in the direction of measurement m. The magnitude of the imaginary vector 2.6 corresponds to a measure of the distance of the target 1.2 from the transmitting/receiving coil system 1.1 normal to the direction of measurement m.

Figure 13:
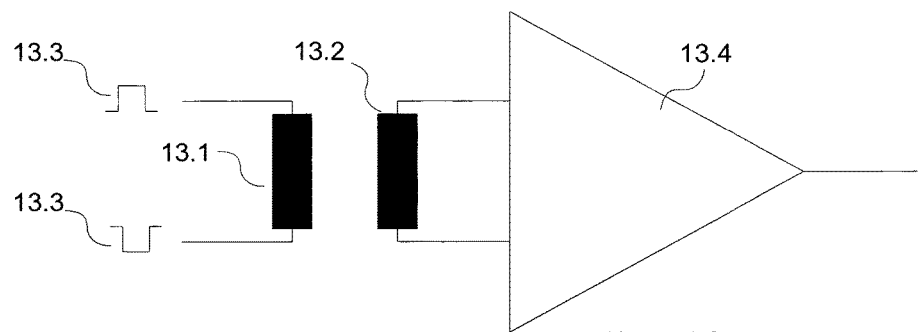
FIG. 13 shows a schematic circuit of a transmitting/receiving coil system having a clock-operated transmitting coil and a receiving coil.
Figure 14A:
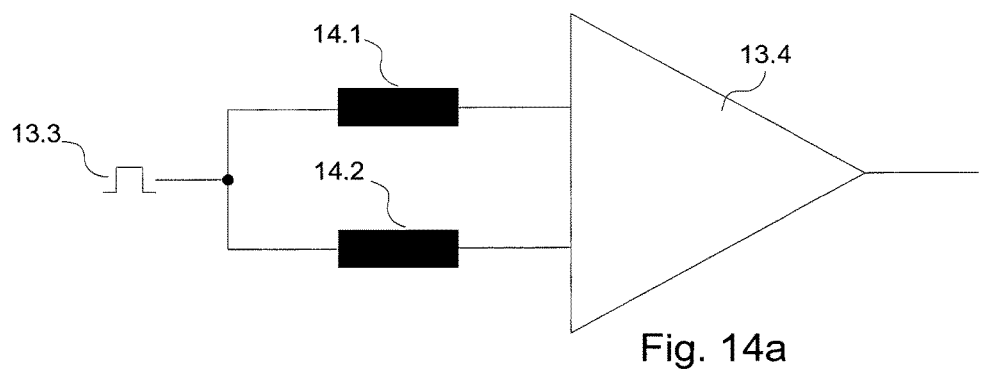
FIGS. 14a, 14b show schematic circuits of alternative transmitting/receiving coil systems.
Figure 14B:
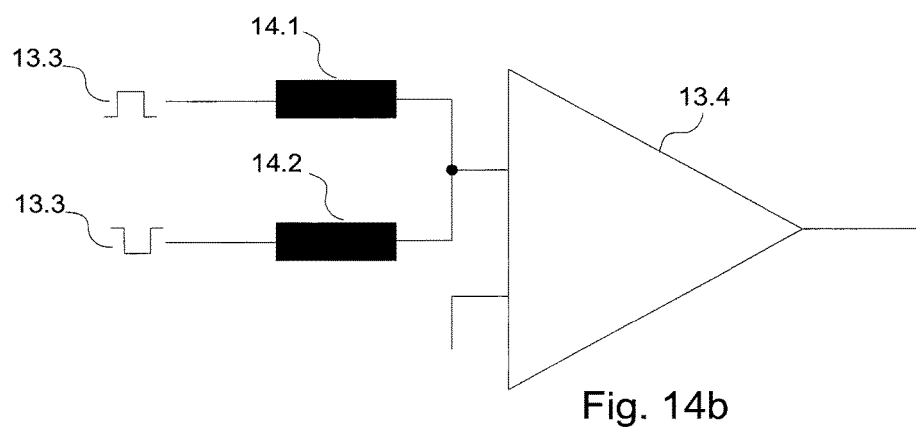

The transmitting/receiving coil system 1.1 may be structured according to FIGS. 13, 14a and 14b. In the exemplary embodiment of FIG. 13, the transmitted signal 13.3 is supplied to the transmitting coil 13.1 in a transmitted clock signal that is alternating and inverted. This transmitted signal induces a received signal in the receiving coil 13.2 which is amplified in the downstream amplifier 13.4 and is then processed in the demodulation 1.8 according to FIG. 1. An arrangement of this kind for the transmitting coil and the receiving coil is not absolutely imperative, however. According to FIG. 14a, the transmitted clock signal may also act on the coils 14.1 and 14.2, which are then simultaneously the transmitting and receiving coil. If a target approaches one of these coils, the transmitted and received magnetic field is affected by the target. The coil 14.2 then becomes the reference coil, while the coil 14.1 for example is affected by the target. This is compensated in the described closed-loop control circuit, from which the control signals to be evaluated for detection of the target are then produced. In FIG. 14b, the coils according to FIG. 14a are supplied with an alternating and inverted transmitted signal 13.3.

For inductive detection of the position of the target 1.2 which is formed in FIGS. 15 and 16 by the targets 15.2, 16.1, the transmitting/receiving coil system 1.1 is provided. In that case too, a transmission driver delivers a periodic transmitted signal 17.1 to the transmitting coil of the transmitting/receiving coil system 1.1. This transmitted signal may be a square signal, according to FIG. 17, but it may also be a sinusoidal signal or any other periodic signal as desired. The transmitting/receiving coil system 1.1 is geometrically shaped and/or calibrated such that when there is no target in the detection region the received signal 17.2 that is emitted from the transmitted signal 1.4 is zero. By contrast, a target in the detection region 10 brings about an inductive effect of a signal not equal to zero in the receive path of the transmitting/receiving coil system 1.1, this signal having a particular amplitude and phase.

The targets according to FIGS. 15 and 16 also have a shape which varies in a direction of measurement m, wherein these exemplary embodiments have in common the fact that the target has a plurality of targets 15.2, 16.1 that taper in the direction of measurement, wherein these targets are arranged such that they taper in opposite directions. The essential criterion is that a plurality of targets having different resonant frequencies are present. In other words, the individual targets take a form such that they affect the signature of the vector in the four-quadrant presentation such that their movement is evaluable without ambiguity. According to FIG. 15, two triangular targets are used, wherein the apices of these triangles point towards one another. The targets are moved together in the direction of measurement m-m in relation to the transmitting/receiving coil system 1.1, which results in the signature according to FIG. 15a. The arrows 15.5 here correspond to individual positions of the target. The longer the arrows, the greater the signal-to-noise ratio, and hence the more clearly the position can be evaluated. This already has the effect that a clear signature is obtained, enabling more exact evaluation with a higher sensitivity of the sensor arrangement. Here, instead of the triangles, rhomboid targets may also be used, as applied in FIG. 16.

It is also conceivable to use a grid pattern which hence does not taper, wherein the patterns of the grid, which resembles the rungs of a ladder, in the short circuits have different capacitances that are evaluable accordingly when the target is moved.

In the exemplary embodiments of FIGS. 15 and 16, the targets 15.2, 16.1 are located on a printed circuit board 15.1 and take the form of printed conductor tracks which are moved together with the printed circuit board in the direction of measurement m. In other words, it is not necessary to use a target having a solid shape, but rather the use of only one or indeed a plurality of parallel conductor tracks is sufficient.

In FIG. 15, two targets 15.2 are created on the printed circuit board 15.1, in the form of conductor tracks. A respective capacitor 15.3, 15.4 is associated with each conductor track. Thus, the conductor tracks form with the capacitor 15.3, 15.4 respective resonant circuits S1, S2, which, specifically in conjunction with the clocked transmitted signal 17.1, similarly results in a corresponding signature according to FIG. 15a. Preferably, the capacitors 15.3, 15.4 are dissimilar, with the result that the targets set up different resonances.

In principle, as illustrated in FIG. 16 by the target 16.1 shown in dashed lines, the targets may be arranged on opposite sides of the printed circuit board 15.1. Here, the target 16.1 takes the form of a rhomboid shape, and together with a capacitor 16.2 similarly forms a resonant circuit S5. The targets 15.2, 16.1 are arranged with their apices in opposite directions and lying partly one above the other, and form a plurality of resonant circuits S3, S4, S5. According to FIG. 16a, an unambiguous signature is produced which clearly shows the difference from previously known signatures. By means of this distinctive signature, a clearly higher sensitivity and hence better evaluation of the detected signals can be achieved.

According to the method, the position of a target is detected using the inductive sensor arrangement. The transmitting/receiving coil system 1.1 is constructed or indeed geometrically shaped and/or calibrated such that the output signal at the output of the transmitting/receiving coil system is a zero signal when there is no metal influence in the detection region 10. If the output signal is a signal not equal to zero, it has a particular amplitude and phase. By way of a closed-loop control circuit having a control signal acting on the receive path, this signal is controlled by a control driver to give the compensated condition even when a target is present in the detection region. The deviations $\Delta x$, $\Delta y$ from the compensated and calibrated condition respectively are inherent in the control signal, as a position or, if required, as an item of information on distance for detecting the position of the target.

Determination of the control signal is performed in that, in a digital evaluation, the amplitude and phase determined at 0° and 180° of the received signals 17.3, 17.4 associated with the two clock phases are controlled to give a zero value in the receive path in a first correction, by means of a correction signal 17.5, in that the phases of the received signals associated with the clock phases are displaced in opposition to one another, as is indicated by the arrow 17.9. In a second correction, the amplitude and phase at 90° and 270° are determined, as shown by the signals 17.6 and 17.7. This results in the correction signal 17.8. If necessary, the signals 17.6 and 17.7 could also be displaced in opposition to one another to bring about a correction signal 17.8. Displacement of the phases of the received signals associated with the clock phases may also be performed by pulse width modulation.

According to FIG. 18, the signals in a microprocessor 18 are processed such that the signals 17.3 and 17.4, which are summed to give the first correction signal 17.5, and the signals 17.6 and 17.7, which are summed to give the correction signal 17.8, occur at the outputs of the microprocessor. The two correction signals then give the final correction C.

The procedure according to the method of displacing the phases of the clock signals in relation to another, and the arrangement and formation of the targets 15.2, 16.1, contribute, both alone and in combination with one another, to further clearly increasing the sensitivity of the sensor arrangement. In practice, a factor of 20 has been found. At the same time, rather than the previously known analogue evaluation, a completely digital evaluation is possible. Instead of controlling the amplitude, the amplitude is kept constant and instead the time segment is varied in order to arrive at the control result.

According to the method, determination of the profile of the deviations $\Delta x$, $\Delta y$ of the control signal is applied in the form of a vector analysis in a phase space of the control signal. The phase space presents, in known manner, a condition of the control signal that is not time-dependent. This may be performed in particular in a four-quadrant presentation of an intersection of xy axes, wherein each point in the phase space corresponds to a possible condition of the control signal that is not time-dependent. Advantageously, for determining the profile, a multiplicity of such points may be determined, which are then advantageously presentable in the phase space in graphical form. The multiplicity of points may, for a particular object, represent a function of the control signal in dependence on distance away. Thus, for example at any desired point in time an instantaneous record of the control signal may be compared with the determined profile. This is advantageously performed in a steady-state condition of the control circuit or controller. Preferably, therefore, first the control circuit and/or controller is started up, or the setpoint value is established. If this results in correspondence and/or approximate correspondence, and provided that only the object is located in the detection region of the sensor unit, it is possible to draw at least qualitative conclusions on the distance away.

It is also possible to determine a profile of this kind as the sensor unit approaches the object, before the object is detected. The term "determine" may be understood to mean that the points of the control signal in the phase space are determined and stored during the approach. This may be performed as soon as the object is detected, that is to say as soon as a point deviating from the unloaded condition occurs in the phase space. This may be performed a plurality of times, with the result that a set of points forming the profile is determinable. In this way, the profile may be determined directly before an actual measurement, that is to say before detection. As an alternative, it is conceivable to determine the profile not directly before detection of the object but in pre-stored tests using a multiplicity of objects, wherein a corresponding profile is storable in a corresponding table for each individual object. During the actual measurement it is then possible, for determination of the profile, not to measure the latter but merely to make a selection from the previously stored table. In this way, the appropriate profile of the control signal in the phase space may also be determined for the currently present object.

A further embodiment of the method is performed by predetermining a threshold value for the profile, comparing the control signal with the threshold value and detecting the object as soon as the control signal deviates far enough from the profile for the threshold value to be exceeded. The term "threshold value" is understood to mean a distance from an individual point and/or from the profile. In particular, this may be an area surrounding the profile, wherein the surrounding area is presentable in the phase space. The term "exceeding the threshold value" is to be understood as moving outside the surrounding area.

Abstracting this to any desired sensor unit, therefore, at least one physical parameter is determined by means of a sensor unit that is excited by at least one periodic excitation 1.4. The sensor unit has at least one detection region 10 in which changes in the parameter in the environment around the sensor unit result in an output signal 1.7 from the sensor unit. The sensor unit is connected such that, if there are no changes in the parameter in the detection region 10, the output signal 1.7 at the output of the sensor unit is a zero signal or a signal approximating to zero, whereas in the event of changes in the parameter in the detection region 10 the output signal 1.7 is a signal not equal to zero and having a particular amplitude and phase. In a closed-loop control circuit, the signal not equal to zero is compensated by a control signal 1.6 to give a zero value in the receive path, even if there are changes in the parameter in the detection region 10, for the purpose of achieving a compensated condition.

If a homogeneous target is used whereof the composition or shape does not vary in the direction of measurement m, according to the claim it is possible to determine, from the item of information contained in the control deviation, the distance of the target from the sensor arrangement, that is to say normal to the direction of measurement m, without performing or needing to perform a measurement in the direction of measurement m. This results in the function of a distance or proximity sensor. The values in or normal to the direction of measurement may thus be determined independently of one another.

It is self-evident that this description may be subject to the broadest possible variety of modifications, changes and adaptations which are within the range of equivalents to the attached claims.

The invention claimed is:

1. A sensor arrangement for inductive or capacitive detection of at least one target by determining at least one physical parameter by means of a sensor unit that is excited by at least one periodic excitation, wherein the sensor unit has at least one detection region in which the at least one target leads to changes in the parameter in the environment around the sensor unit and thus results in an output signal from the sensor unit,
  wherein the sensor unit is connected such that, if there are no changes in the at least one physical parameter in the detection region, the output signal at the output of the sensor unit is a zero signal, whereas in the event of changes in the at least one physical parameter in the detection region the output signal is a signal not equal to zero and having a particular amplitude and phase,
  wherein in a closed-loop control circuit, the signal not equal to zero is compensated to give a zero value by a control signal in a receive path, even if there are changes in the at least one physical parameter in the detection region, for the purpose of achieving a compensated condition,
  wherein a deviation in the control signal, required for the purpose of achieving the compensated condition, from a compensated initial condition, as an item of information on the parameter, is inherent in the control signal,
  wherein a device for signal preparation for performing a vector analysis in a phase space of the deviation in the control signal is provided, by means of which an imaginary vector in an x, y coordinate system is obtained, which imaginary vector leads from the origin of the x, y coordinate system, which corresponds with the compensated initial condition, to a measurement point,
  wherein at least one of
    a first measurement variable is determinable by an angle of the imaginary vector with an x axis of the x, y coordinate system, or
    a second measurement variable is determinable by a magnitude of the imaginary vector.

2. A sensor arrangement according to claim 1, wherein the controller is a continuous controller.

3. A sensor arrangement according to claim 1, wherein a shape or composition of the at least one target is detectable, the shape or composition varying in a direction of measurement.

4. A sensor arrangement according to claim 1, wherein an arcuate, tapering target or a rotationally symmetrical, conical target is detectable as the at least one target.

5. A sensor arrangement according to claim 1, wherein a plurality of targets are provided that have different resonant frequencies and take a form such that they affect a signature of a vector plot in the four-quadrant presentation such that their movement is unambiguously evaluable.

6. A sensor arrangement according to claim 1, wherein a target is detectable which has a plurality of targets that taper in the direction of measurement and taper in opposed directions.

7. A sensor arrangement according to claim 1, wherein the at least one target is formed by printed conductor tracks that are arranged on a printed circuit board.

8. A sensor arrangement according to claim 1, wherein the at least one target is a resonant circuit.

9. A sensor arrangement according to claim 8, wherein with a plurality of targets the resonant circuits are arranged on opposite sides of a printed circuit board.

10. A sensor arrangement according to one of claim 1, wherein the at least one target is mounted on the periphery of a rotational body.

11. A sensor arrangement according to claim 10, wherein a plurality of targets are mounted offset spatially and in respect of their angular position on the rotational body.

12. A sensor arrangement according to claim 1, wherein the first measurement variable is ascertainable as a movement or a position or a form or a composition of the target along a direction of measurement and the second measurement variable is separately ascertainable as a distance or a movement of the target normal to the direction of measurement.

13. A sensor arrangement for inductive or capacitive detection of at least one target by determining at least one physical parameter by means of a sensor unit that is excited by at least one periodic excitation, wherein the sensor unit has at least one detection region in which the at least one target leads to changes in the parameter in the environment around the sensor unit and thus results in an output signal from the sensor unit,
   wherein the sensor unit is connected such that, if there are no changes in the at least one physical parameter in the detection region, the output signal at the output of the sensor unit is a zero signal, whereas in the event of changes in the at least one physical parameter in the detection region the output signal is a signal not equal to zero and having a particular amplitude and phase,
   wherein in a closed-loop control circuit, the signal not equal to zero is compensated to give a zero value by a control signal in a receive path, even if there are changes in the at least one physical parameter in the detection region, for the purpose of achieving a compensated condition,
   wherein a deviation in the control signal, required for the purpose of achieving the compensated condition, from a compensated initial condition, as an item of information on the parameter, is inherent in the control signal,
   wherein for a device for signal preparation for performing a vector analysis in a phase space of the deviation in the control signal, by means of which an imaginary vector in an x, y coordinate system is obtained, which imaginary vector leads from the origin of the x, y coordinate system, which corresponds with the compensated initial condition, to a measurement point,
   wherein at least one of,
      as an item of information, a distance of the at least one target from the sensor arrangement is ascertainable by a magnitude of the imaginary vector, or
      as an additional item of information, that is superimposed to the item of information, an angle of the imaginary vector with an x axis of the x, y coordinate system is ascertainable.

14. A sensor arrangement according to claim 13, wherein the physical parameter is determined for the inductive detection of one of a position or a movement of the at least one target, and wherein at least one transmitting/receiving coil system is provided, which is formed by at least two coils, comprises the detection region and is connected such that in the absence of the influence of metal in the detection region an output signal at an output of the transmitting/receiving coil system is the zero signal,
   wherein if there is the at least one target in the detection region, the output signal at the output of the transmitting/receiving coil system is the signal that is not equal to zero and has the particular amplitude and phase,
   and having a controller for the closed-loop control circuit whereof the control signal adjusts the signal that is not equal to zero in the receive path to give a zero value even in a presence of the at least one target in the detection region, for the purpose of achieving the compensated condition,
   wherein the deviation of the control signal from the compensated condition, as distance information for detection of the position of the at least one target, is inherent in the control signal,
   wherein the magnitude of the imaginary vector is a measure of the distance of the at least one target from the transmitting/receiving coil system normal to the direction of measurement as the item of information, and
   wherein the angle that the imaginary vector makes with the x axis is a measure of the movement of the at least one target in the direction of measurement as the additional item of information.

15. A sensor arrangement according to claim 14, wherein the controller is a continuous controller.

16. A sensor arrangement according to claim 14, wherein a shape or composition of the at least one target is detectable, the shape or composition varying in the direction of measurement.

17. A sensor arrangement according to claim 13, wherein an arcuate, tapering target or a rotationally symmetrical, conical target is detectable as the at least one target.

18. A sensor arrangement according to claim 13, wherein a plurality of targets are provided that have different resonant frequencies and take a form such that they affect a signature of a vector plot in the four-quadrant presentation such that their movement is unambiguously evaluable.

19. A sensor arrangement according to claim 13, wherein a target is detectable which has a plurality of targets that taper in the direction of measurement and taper in opposed directions.

20. A sensor arrangement according to claim 13, wherein the at least one target is formed by printed conductor tracks that are arranged on a printed circuit board.

21. A sensor arrangement according to claim 13, wherein the at least one target is a resonant circuit.

22. A sensor arrangement according to claim 21, characterized in that with a plurality of targets the resonant circuits are arranged on opposite sides of a printed circuit board.

23. A sensor arrangement according to claim 14, wherein the transmitting/receiving coil system includes at least two transmitting/receiving coil systems that are arranged at different rotational angle positions of the target.

24. A sensor arrangement according to claim 23, wherein two transmitting/receiving coil systems are located diametrically opposite one another in relation to an axis of rotation of the at least one target.

25. A sensor arrangement according to claim 23, wherein the at least one target is mounted on the periphery of a rotational body.

26. A sensor arrangement according to claim 25, wherein a plurality of targets are mounted offset spatially and in respect of their angular position on the rotational body.

27. A sensor arrangement according to claim 13, wherein the additional item of information is ascertainable as a movement or a position or a form or a composition of the target along the direction of measurement and the item of information is separately ascertainable from a distance or a movement of the target normal to the direction of measurement.

28. A method for inductive or capacitive determining at least one physical parameter by means of a sensor unit that is excited by at least one periodic excitation, wherein the sensor unit has at least one detection region in which at least one target leads to changes in the at least one physical parameter in an environment around the sensor unit and thus results in an output signal from the sensor unit,
wherein the sensor unit is connected such that, if there are no changes in the at least one physical parameter in the detection region, the output signal at an output of the sensor unit is a zero signal, whereas in the event of changes in the at least one physical parameter in the detection region the output signal is a signal not equal to zero and having a particular amplitude and phase,
wherein in a closed-loop control circuit, the signal not equal to zero is compensated to give a zero value by a control signal in the receive path, even if there are changes in the at least one physical parameter in the detection region, for the purpose of achieving a compensated condition,
wherein a deviation in the control signal, required for the purpose of achieving the compensated condition, from an initial condition, as an item of information on the parameter, is inherent in the control signal,
wherein a vector analysis of the deviation of the control value is performed in a phase space, thereby obtaining an imaginary vector in an x, y coordinate system, which imaginary vector leads from the origin of the x, y coordinate system, which corresponds with the compensated initial condition, to a measurement point,
wherein at least one of
a first measurement variable is determined by an angle of the imaginary vector with an x axis of an x, y coordinate system, or
a second measurement variable is determined by a magnitude of the imaginary vector.

29. A method according to claim 28, wherein a shape or composition that varies in a direction of measurement is used as the at least one target.

30. A method according to claim 28, wherein the signal not equal to zero is continuously compensated to give a zero value, for the purpose of achieving a compensated condition.

31. A method for inductive or capacitive determining at least one physical parameter by means of a sensor unit that is excited by at least one periodic excitation, wherein the sensor unit has at least one detection region in which at least one target leads to changes in the at least one physical parameter in an environment around the sensor unit and thus results in an output signal from the sensor unit,
wherein the sensor unit is connected such that, if there are no changes in the at least one physical parameter in the detection region, the output signal at the output of the sensor unit is a zero signal, whereas in the event of changes in the at least one physical parameter in the detection region the output signal is a signal not equal to zero and having a particular amplitude and phase,
wherein in a closed-loop control circuit, the signal not equal to zero is compensated to give a zero value by a control signal in a receive path, even if there are changes in the parameter in the detection region, for the purpose of achieving a compensated condition,
wherein a deviation in the control signal, required for the purpose of achieving the compensated condition, from an initial condition, as an item of information on the parameter, is inherent in the control signal,
wherein a vector analysis of the deviation of the control signal is performed in a phase space, thereby obtaining an imaginary vector in an x, y coordinate system, which imaginary vector leads from the origin of the x, y coordinate system, which corresponds with the compensated initial condition, to a measurement point,
wherein at least one of,
as an item of information, a distance of a target from the sensor arrangement is ascertained by a magnitude of the imaginary vector, or
as an additional item of information, that is superimposed to the item of information, an angle of the imaginary vector with an x axis of the x, y coordinate system is ascertained.

32. A method according to claim 31, wherein for inductive detection of the position or movement of the at least one target there is used a sensor arrangement having a transmitting/receiving coil system which is formed by at least two coils, has the detection region and is connected such that in the absence of the influence of metal in the detection region the output signal at the output of the transmitting/receiving coil system is the zero signal,
wherein if there is the at least one target in the detection region, the output signal at the output of the transmitting/receiving coil system is the signal that is not equal to zero and has the particular amplitude and phase,
wherein, in the closed-loop control circuit, the signal that is not equal to zero is compensated by the control signal in the receive path to give a zero value even in the presence of the at least one target in the detection region, for the purpose of achieving a compensated condition,
wherein the deviation of the control signal from the compensated condition, as distance information for detection of the position of the at least one target, is inherent in the control signal,
wherein the magnitude of the imaginary vector is a measure of the distance of the at least one target from the transmitting/receiving coil system normal to the direction of measurement as the item of information, and
wherein the angle of that imaginary vector makes with the x axis is a measure of the movement of the at least one target in the direction of measurement as the additional item of information, and
wherein the angle that the imaginary vector makes with the x axis is a measure of the movement of the at least one target in the direction of measurement as the additional item of information.

33. A method according to claim 32, wherein a shape or composition that varies in a direction of measurement is used as the at least one target.

34. A method according to claim 31, wherein the signal not equal to zero is continuously compensated to give a zero value, for the purpose of achieving a compensated condition.

35. A method according to claim 31, wherein the additional item of information is ascertained as a movement or a position or a form or a composition of the target along the direction of measurement and the item of information is separately ascertained from a distance or a movement of the target normal to the direction of measurement.

\* \* \* \* \*